United States Patent [19]

Browne

[11] Patent Number: Plant 6,690

[45] Date of Patent: Mar. 21, 1989

[54] *DRACAENA DEREMENSIS* NAMED KERRY

[76] Inventor: Kermit C. Browne, 500 Royal St., Waxahachie, Tex. 75165

[21] Appl. No.: 94,905

[22] Filed: Sep. 10, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new *Dracaena deremensis* cultivar named Kerry having intense dark green foliage color, wide and thick leaves, strong growth habit, and quick rooting.

1 Drawing Sheet

1

The present invention comprises a new and distinctive cultivar of Dracaena plant, botanically known as *Dracaena deremensis,* and known by the cultivar name Kerry.

The new cultivar Kerry is a sport of the *Dracaena deremensis* cultivar known by the varietal name Jumbo. In turn, Jumbo is a sport of the well-known Dracaena cultivar Warneckei, a variegated gray-green cultivar.

Applicant discovered the new cultivar growing in a cultivated area in Barranquitas, Puerto Rico, in the summer of 1985. The new cultivar was growing in an outdoor field with plants of the parent cultivar Jumbo, and was distinguishable from Jumbo by its wider leaves, solid dark green leaf color, and by its significantly thicker leaves. The new cultivar Kerry also seemed to display a stronger growth habit.

After observing the growth of the newly discovered sport for some time, during which it reached a height of approximately five (5) feet and its unique characteristics were continually made evident, tip cuttings were taken under my direction and supervision in Barranquitas, Puerto Rico, in the fall of 1986. The observed growth of these cuttings has demonstrated that the combination of characteristics as disclosed herein for Kerry are firmly fixed and are retained through successive generations of asexual reproduction. Kerry has not been observed under all possible environmental conditions. The phenotype may vary with variations in environment such as temperature, light intensity, daylength, and the like. The following observations, measurements and comparisons describe plants grown in Barranquitas, Puerto Rico, in outdoor field conditions.

The following characteristics have been repeatedly observed and are determined to be basic characteristics of Kerry, which in combination distinguish this new Dracaena as a new and distinct cultivar:

(1) The leaves are a much darker and more intense green than the leaf color of the parent cultivar Jumbo, which is variegated, with the white pigmentation creating a gray-green emerald color.

(2) The leaf is substantially wider than the leaves of the parent cultivar Jumbo, being as wide as 3.5 inches at its widest point.

(3) The thickness of the leaves is greater than the thickness of any of the cultivars above referred to, including the parent. Although no micrometer comparisons have been made, the increased thickness of the leaf of Kerry is immediately recognizable by feel, and gives the leaf a more leather-like appearance and feel.

2

(4) The stem of the plant is relatively large and strong, and gives the plant excellent strength and rigidity.

(5) Based on propagation to date, the ease of propagation has been very good, with the rootings being heavy and developing very quickly.

Although Kerry is a sport of Jumbo, the closest comparison cultivar is Janet Craig. In comparison to Janet Craig, the leaves of Kerry are thicker, wider, and darker green in color, and the stem is substantially larger. In addition, Kerry is a much stronger grower than Janet Craig. The leaf color of Kerry is also darker than the leaves of Janet Craig Compacta, a sport of Janet Craig having somewhat deeper green leaves than its parent. The leaf form of Janet Craig Compacta also varies from the leaf form of Kerry.

The accompanying photographic drawings show typical foliage and growth characteristics of the new cultivar. The photograph appearing at the top of the sheet is a perspective top view showing the new cultivar grown in a 4-inch pot. The photograph appearing at the bottom of the sheet is an enlarged perspective view of the upper portion of the plant illustrated in the top photograph.

In the following description, color references are made to The Royal Horticultural Society Colour Chart (R.H.S.), except where general colors of ordinary significance are referred to. Color values were taken directly from a plant of Kerry under a combination of natural and fluorescent light at approximately mid-day in Alexandria, Va. in August. The plant described and illustrated in the photographs is approximately 3–4 months old.

Classification:

*Botanical.*—*Dracaena deremensis* cv. Kerry.

*Commercial.*—Dracaena.

Propagation: By tip cuttings which root quickly and easily.

Plant: Herbaceous.

*Form.*—Straight and erect. The leaves are regularly spaced and retain a substantial horizontal bent, thereby creating a full, symmetrical appearance; very strong grower.

*Size.*—Fully mature plants (4–5 years) will reach heights of twelve (12) feet or more if allowed to freely grow. Kerry possesses a strong growth habit, and growth rate is somewhat above average. The plants shown in the photographs are approximately 3–4 months old, although the strong and erect growth habits are clearly evident.

*Leaves.*—Size: Mature leaves are 20–22″ in length and typically 3.25 to 3.5″ in width at their widest point, which is normally 6–8″ from end of leaf. Shape: Generally lanceolate, although leaf is widest more closely adjacent the tip than the base; tip is acute, with last 3–4″ of tip narrowing gradually to a point; center leaves are very erect, with erectness diminishing toward base; intermediate leaves have more horizontal orientation with the tips extending downwardly, and the bottom leaves are arched and reversed. The margins of the leaves are slightly wavy, and the edges of the leaves are smooth. Texture: The leaves have a leathery feel primarily because of their thickness. The leaves are very noticeably thicker than the leaves of both Janet Craig and Jumbo. Striations are recognizable on under surface which extend generally parallel to midrib; striations only barely visible on upper surface. Color: Upper surface: 139A (By contrast, the color of the upper surface of the leaves of Janet Craig is approximately 137A-B, and Jumbo, being variegated, is a much lighter gray-green.) The color of Kerry is a uniform intense dark green (139A), with no variegation. Under surface: 137A-B, midrib slightly lighter.

I claim:

1. A new and distinct cultivar of Dracaena named Kerry, as illustrated and described, and parts thereof.

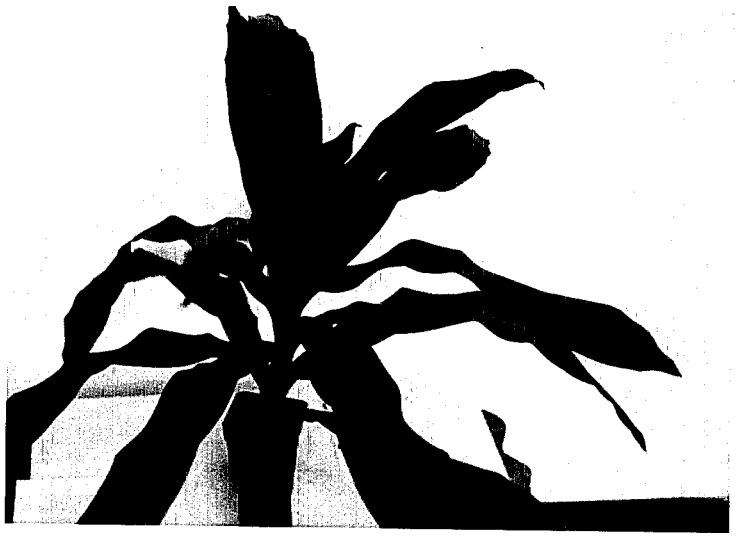
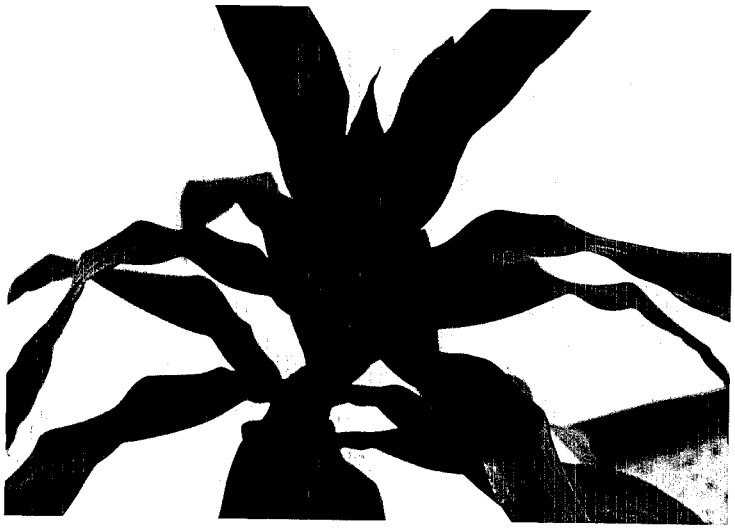

* * * * *